US009539179B2

(12) United States Patent
Cano et al.

(10) Patent No.: US 9,539,179 B2
(45) Date of Patent: Jan. 10, 2017

(54) INTERACTIVE KIOSK FOR COUNTING, LABELING, AND SHIPPING OF RECALLED MEDICATION CAPSULES

(71) Applicant: QUALANEX, LLC, Gurnee, IL (US)

(72) Inventors: Derek Cano, Broomfield, CO (US); Donald W. Stark, Arvada, CO (US); Alan Lewis Dubois, Louisville, CO (US)

(73) Assignee: QUALANEX, LLC, Gurnee, IL (US)

( * ) Notice: Subject to any disclaimer, the term of this patent is extended or adjusted under 35 U.S.C. 154(b) by 0 days.

(21) Appl. No.: 14/805,370

(22) Filed: Jul. 21, 2015

(65) Prior Publication Data

US 2016/0143813 A1 May 26, 2016

Related U.S. Application Data

(60) Provisional application No. 62/027,179, filed on Jul. 21, 2014.

(51) Int. Cl.
G06F 19/00 (2011.01)
A61J 7/02 (2006.01)
G07F 17/00 (2006.01)

(52) U.S. Cl.
CPC ............ *A61J 7/02* (2013.01); *G06F 19/3462* (2013.01); *G07F 17/0092* (2013.01)

(58) Field of Classification Search
CPC .................................. A61J 7/02; G06F 19/3462
See application file for complete search history.

(56) References Cited

U.S. PATENT DOCUMENTS

| 5,884,806 | A  | * | 3/1999  | Boyer    | A61J 7/02    |
|           |    |   |         |          | 221/13       |
| 6,711,460 | B1 | * | 3/2004  | Reese    | G06F 19/3456 |
|           |    |   |         |          | 700/216      |
| 7,599,516 | B2 | * | 10/2009 | Limer    | G06M 11/00   |
|           |    |   |         |          | 211/88.01    |
| 7,930,064 | B2 | * | 4/2011  | Popovich, Jr. | G07F 17/0092 |
|           |    |   |         |          | 221/2        |
| 8,271,128 | B1 | * | 9/2012  | Schultz  | A61J 7/02    |
|           |    |   |         |          | 700/236      |
| 8,374,887 | B1 | * | 2/2013  | Alexander | G06Q 10/0633 |
|           |    |   |         |          | 700/216      |
| 8,827,112 | B2 | * | 9/2014  | Yuyama   | A61J 7/02    |
|           |    |   |         |          | 221/224      |

(Continued)

*Primary Examiner* — Timothy Waggoner
(74) *Attorney, Agent, or Firm* — Foley & Lardner LLP (57) ABSTRACT

A kiosk according to an embodiment of the present invention includes a housing; a touch screen configured to receive input information from a user; a label printer configured to print output information from the kiosk; a pill drop opening; a pill chute; a drive tube having entry and exit openings, wherein the drive tube has an axis extending through a longitudinal axial centerline thereof, and has an inside surface comprising a helical flute, wherein the entry opening is in communication with the pill chute, and wherein the exit opening is higher than the entry opening such that the axial centerline of the drive tube is inclined; a motor configured to rotate the drive tube to separate and convey pills received through the pill drop opening and the pill chute; and an optical counter configured to count the pills as the pills fall from the exit opening of the drive tube.

18 Claims, 9 Drawing Sheets

(56) References Cited

U.S. PATENT DOCUMENTS

| | | | |
|---|---|---|---|
| 8,833,602 B1 * | 9/2014 | Balasubramanian | A61J 7/02 221/203 |
| 9,033,006 B2 * | 5/2015 | Perazzo | A61J 7/0053 141/319 |
| 2004/0088187 A1 * | 5/2004 | Chudy | G06Q 10/10 705/2 |

* cited by examiner

INTERACTIVE KIOSK FOR COUNTING, LABELING, AND SHIPPING OF RECALLED MEDICATION CAPSULES

CROSS-REFERENCES

This application claims the benefit of U.S. Provisional Patent Application No. 62/027,179 filed on Jul. 21, 2014, which is hereby incorporated by reference in its entirety.

TECHNICAL FIELD

Embodiments described herein relate generally to an interactive kiosk for receiving medication, and more specifically to an interactive kiosk for receiving, counting, and labeling medication liquids and capsules.

BACKGROUND

When a pharmacy or other organization accepts recalled or partially used pharmaceutical prescriptions, it is often a time-consuming process to verify the medication, count the number of pills or volume of liquid being returned, and address and ship the medication to the origin company or its designated recall agent. Various different information systems are employed for different parts of this process, often requiring a high level of supervision and manual intervention, thus increasing expense.

SUMMARY

A kiosk according to an embodiment of the present invention includes a housing; a touch screen on the housing, the touch screen configured to receive input information from a user of the kiosk; a label printer on the housing, the label printer configured to print output information from the kiosk; a pill drop opening; a pill chute; a drive tube having an entry opening and an exit opening, wherein the drive tube is tubular, has an axis extending through a longitudinal axial centerline of the drive tube, and has an inside surface comprising a helical flute, wherein the entry opening is in communication with the pill chute, and wherein the exit opening is higher than the entry opening such that the axial centerline of the drive tube is inclined; a motor configured to rotate the drive tube to separate and convey pills received through the pill drop opening and the pill chute; and an optical counter configured to count the pills as the pills fall from the exit opening of the drive tube.

A kiosk according to an embodiment of the present invention may includes a processor within the housing, the processor communicably coupled to the touch screen, the label printer, the motor, and the optical counter, wherein the processor is configured to: receive information about the pills from the touch screen based upon user input; selectively actuate the motor to convey the pills from the entry opening to the exit opening; receive and store count information about a number of the pills from the optical counter; and instruct the label printer to print a label displaying the count information.

A kiosk according to an embodiment of the present invention may further include a camera; and a scale, wherein the processor further communicably coupled to the camera and the scale, and wherein the processor is further configured to: receive information about a liquid medicine; receive and store information about a weight of the liquid medicine from the scale while the liquid medicine is placed upon the scale; receive and store visual information from the camera about the liquid medicine while the liquid medicine is placed upon the scale.

According to some embodiments of the present invention, the axial centerline of the drive tube is inclined along a direction from a rear of the kiosk toward a front of the kiosk. In some cases, the touch screen is located at the front of the kiosk. The kiosk may include a catch bin located at the front of the kiosk, wherein the catch bin is configured to receive the pills after the pills have fallen from the exit opening of the drive tube, according to embodiments of the present invention. While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIGS. 1-5 illustrate external views of a kiosk 10 that facilitates receiving, counting, labeling, and shipping returned medications. The kiosk 10 includes a housing 11, a pill drop opening 12, as well as a touch screen 14 configured to permit a user to enter information about the medicine being returned. Kiosk 10 further includes a finger scanner 16 and a front-facing camera 18 to permit the kiosk 10 to document and/or authenticate the user of the kiosk 10. Kiosk 10 further includes a two-dimensional bar code scanner 17 configured to receive bar code information, for example from the labels of medicines being processed by the kiosk 10. The kiosk 10 may further include a first label printer 20 and/or a second label printer 22, as well as a catch bin 24 that is removable from the housing 11 for collecting pills after they have been inserted through pill drop opening 12 and counted.

Figure 1:
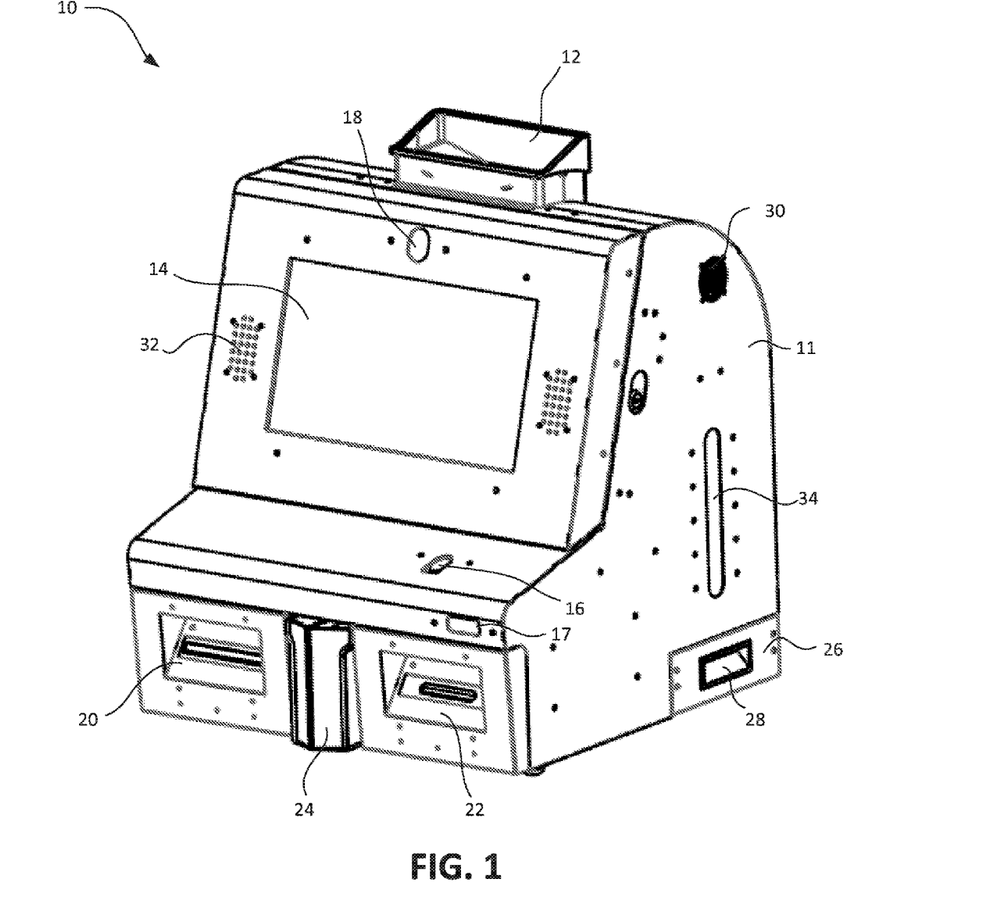
FIG. 1 illustrates a front perspective view of an interactive kiosk according to embodiments of the present invention.
Figure 2:
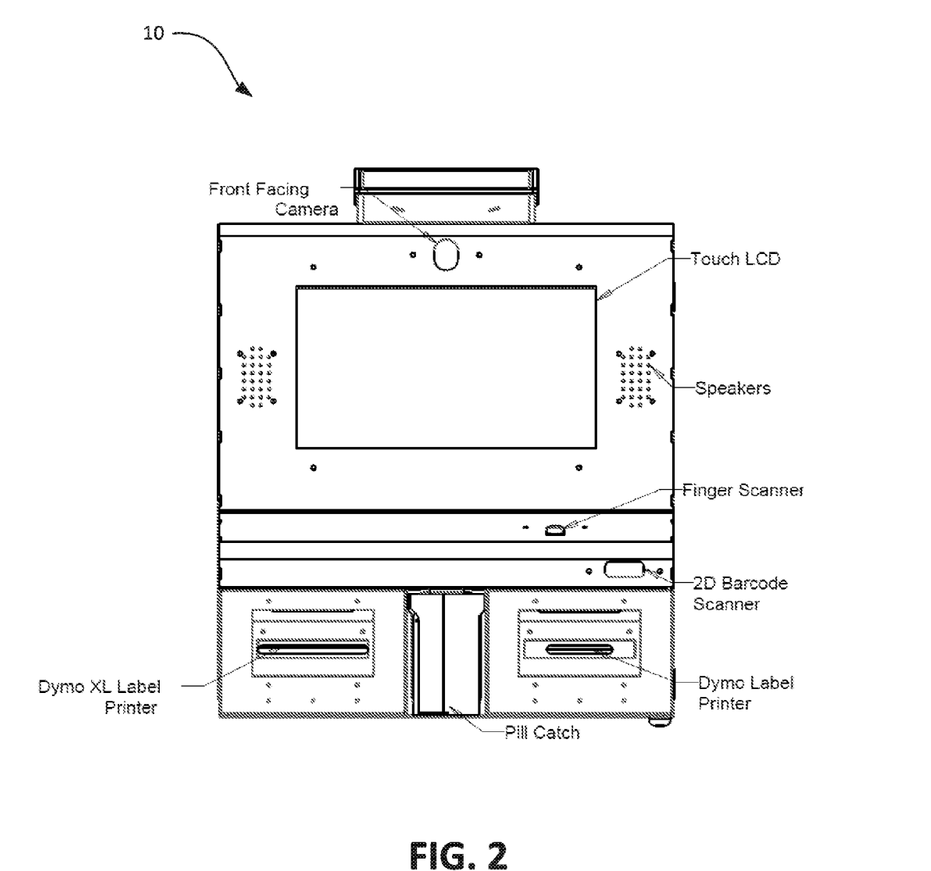
FIG. 2 illustrates a front elevation view of the interactive kiosk of FIG. 1, according to embodiments of the present invention.
Figure 3:
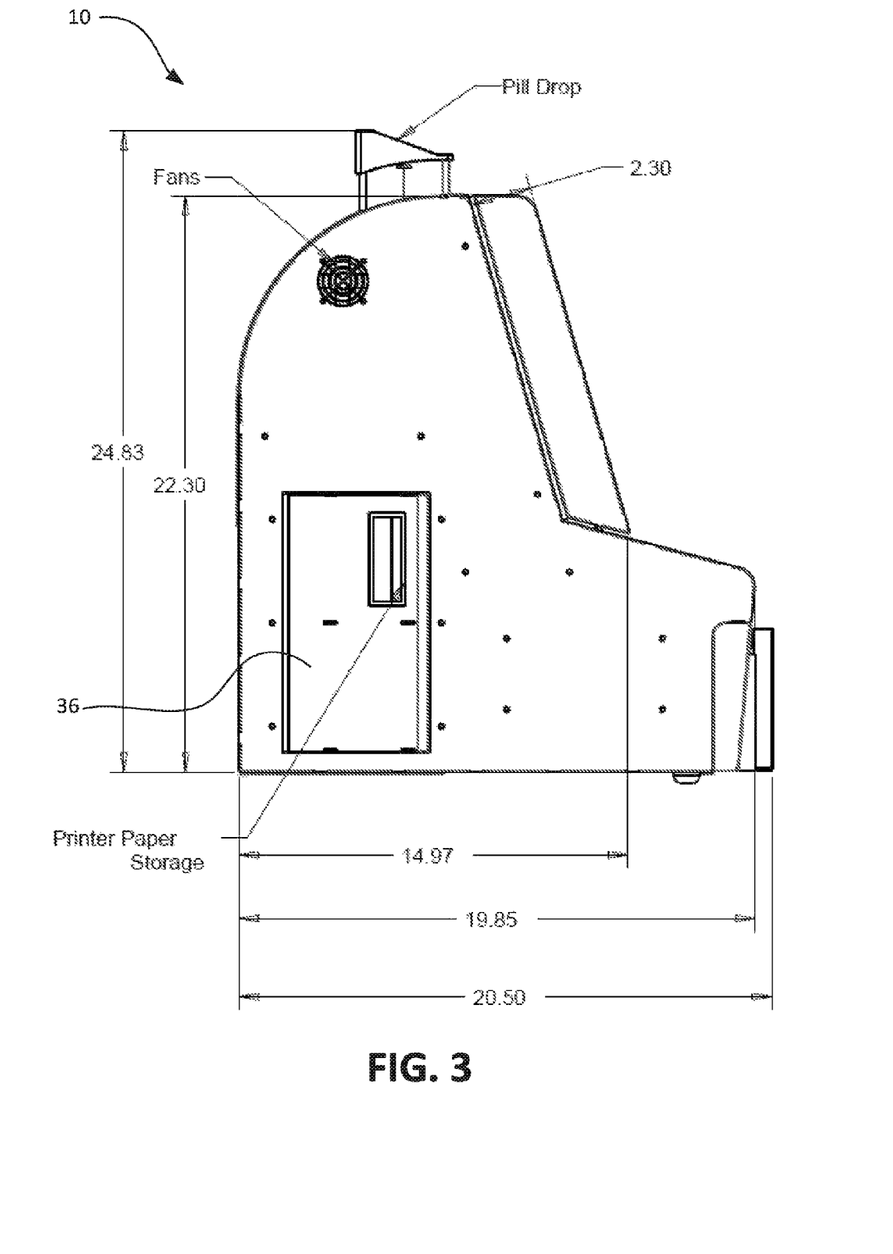
FIG. 3 illustrates a left side elevation view of the interactive kiosk of FIGS. 1 and 2, according to embodiments of the present invention
Figure 4:
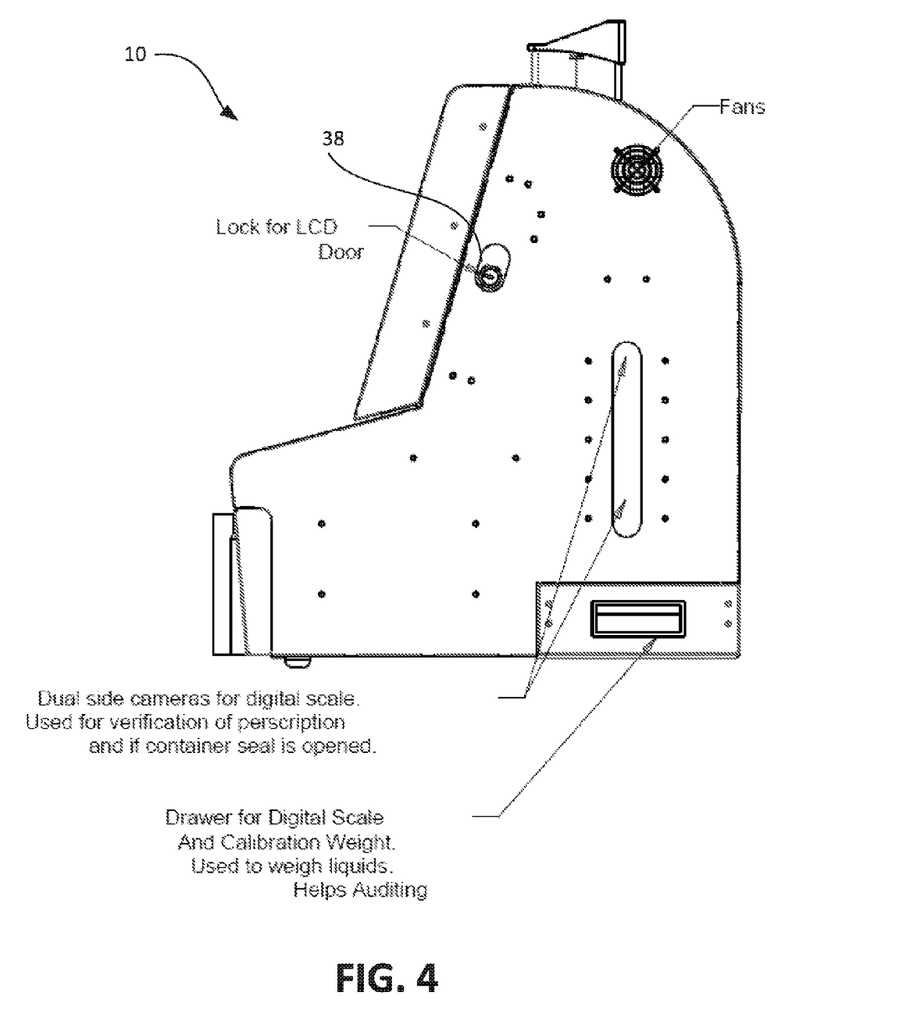
FIG. 4 illustrates a right side elevation view of the interactive kiosk of FIGS. 1-3, according to embodiments of the present invention.

The kiosk 10 may further include a side drawer 26, with a handle 28, which slides in and out of housing 11. The side drawer 26 may include a scale 68 (see FIG. 8) for weighing liquid medicines. The side drawer 26 may further include a calibration weight (not shown) used for calibrating the scale 68. The kiosk 10 may further include a vent 30 configured to permit active or passive cooling or ventilation of the housing 11. Kiosk may further include a front speaker 32 for conveying audio information to the user. Dual side cameras may be mounted on or within camera mount 34, which may be used by kiosk 10 to verify medicine placed upon the digital scale 68 within the side drawer 26, as well as to document whether the seal of the medicine container placed upon the scale is damaged or opened. As shown in FIG. 4, the touch screen 14, which may be an LCD device, may be accessed via a hinged door, which may be locked at lock 38, according to embodiments of the present invention.

Figure 5:
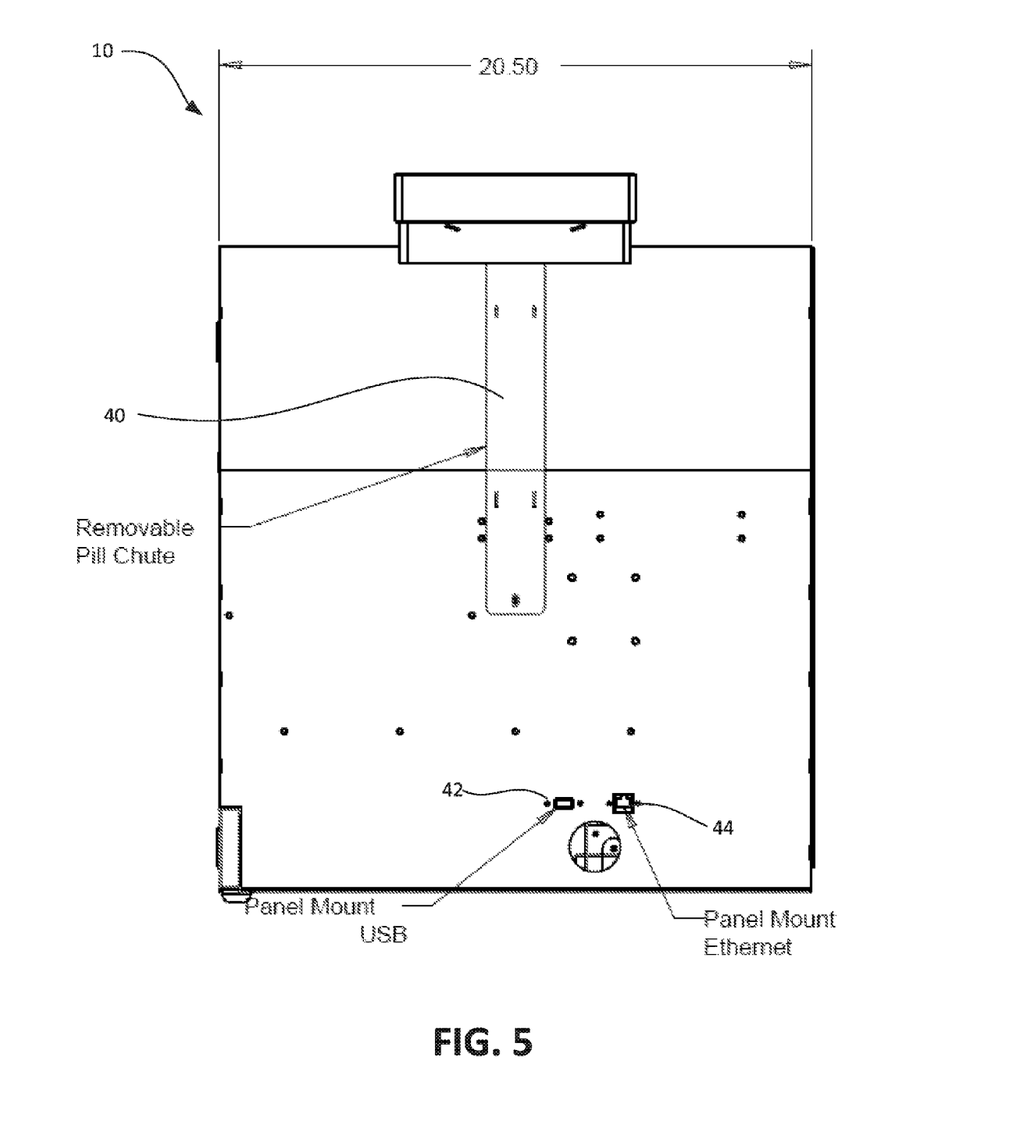
FIG. 5 illustrates a rear elevation view of the interactive kiosk of FIGS. 1-4, according to embodiments of the present invention.

As illustrated in FIG. 5, the rear of the housing 11 may include a pill chute 40 which is removable for maintenance, cleaning, and/or unjamming. The kiosk 10 may further include communications ports such as a USB port 42 and/or an Ethernet port 44, according to embodiments of the present invention.

Figure 6:
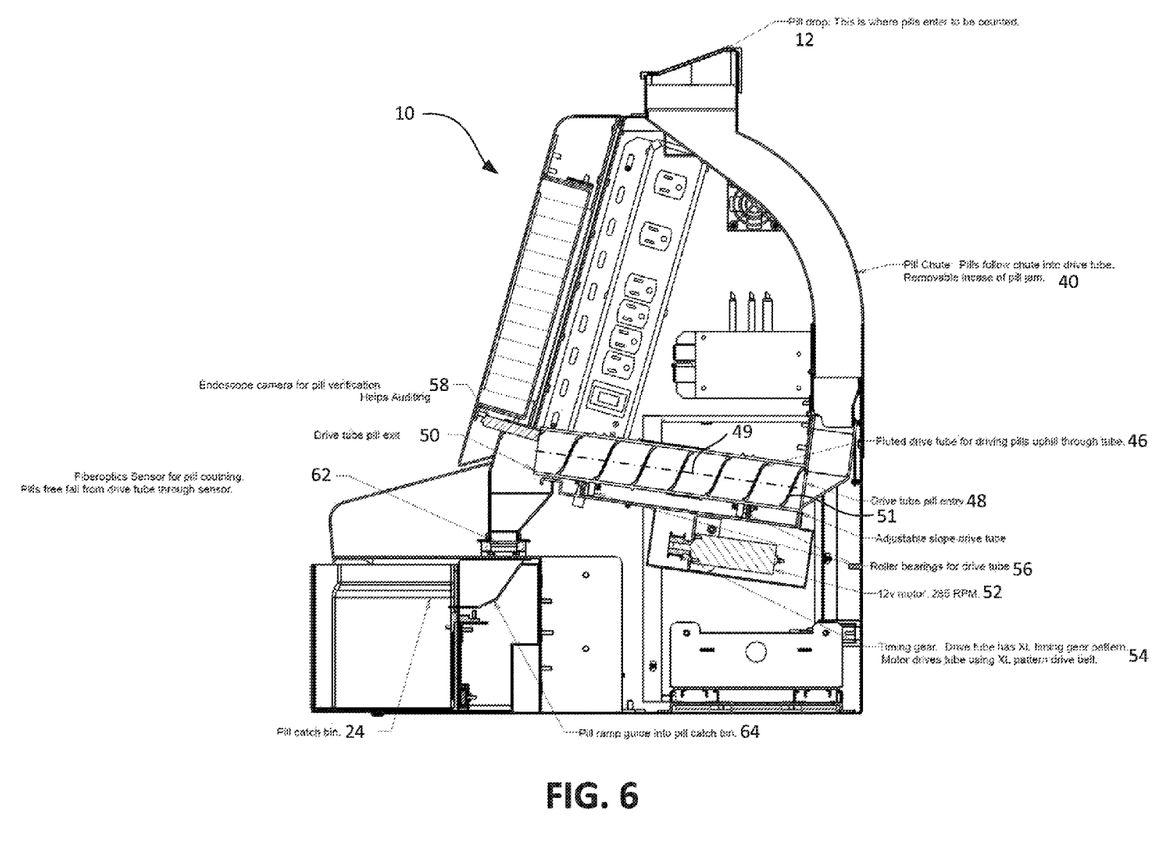
FIG. 6 illustrates a right side elevation cross-sectional view of the interactive kiosk of FIGS. 1-5, according to embodiments of the present invention.
Figure 7:
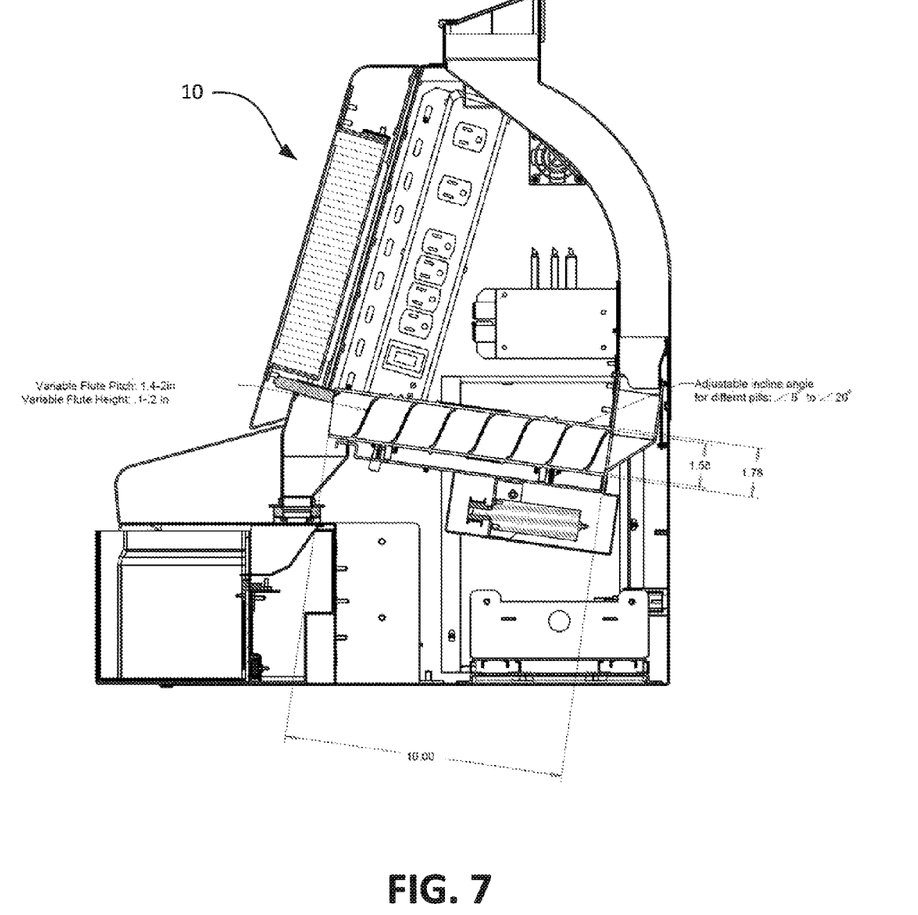
FIG. 7 illustrates the right side elevation cross-sectional view of the interactive kiosk of FIGS. 1-6 showing additional detail, according to embodiments of the present invention.

FIGS. 6 and 7 illustrate a cross-sectional view of kiosk 10 taken along a midline of the kiosk 10, according to embodiments of the present invention. FIGS. 6 and 7 illustrate the operation of the pill receiving and counting system of the kiosk 10. Once the kiosk 10 has received information about the pills to be received, for example via touch screen 14, the kiosk 10 instructs the user to drop the pills into the pill drop opening 12, for example by opening any bottle in which the pills are contained and pouring the pills into the pill drop opening 12. From the pill drop opening 12, the pills fall through the pill chute 40 until they gather at or near the entry opening 48 of the drive tube 46. A motor 52 is used to drive rotation of the drive tube 46, with a timing gear system 54 used to couple the motor 52 with the drive tube 46 for rotation of the drive tube 46 by the motor 52. The drive tube 46 is mounted upon roller bearings 56 to permit rotation of the drive tube 46 with respect to the housing 11. The motor may be, for example, a twelve-volt motor with a rotational speed of 285 rotations per minute, according to embodiments of the present invention.

As the drive tube 46 is rotated about its central axis 49, which may also be referred to as axial centerline 49, pills fall, via gravity, from pill chute 40 into drive tube 46 through entry opening 48. As shown in FIGS. 6 and 7, the drive tube 46 has an exit opening 50, and exit opening 50 is inclined relative to entry opening 48. The inside surface of the drive tube 46 includes a flute 51 which separates pills from piles or stacks formed near the entry opening 48 and conveys the pills, for example one-at-a-time, upwardly toward the exit opening 50. This helps to spread out the pills to make them easier to count. A camera 58, for example an endoscope camera, helps the kiosk 10 to verify pills, and may record images that may be used to assist in auditing the performance of kiosk 10 and/or its users. It has also been found that the use of a drive tube with an internal flute 51 with the exit opening 50 inclined with respect to the entry opening 48 permits the same drive tube 46 to be used for multiple different pill shapes and sizes. Once the pills are conveyed to the exit opening 50 via rotation of the drive tube 46, the pills fall out of exit opening 50 and through (and/or past) a fiber optic sensor 62 for pill counting. For example, the pills free fall through fiber optic sensor 62, according to embodiments of the present invention. Next, the pills fall onto a pill ramp guide 64 which directs the pills to a catch bin 24. After the pills have been counted, the kiosk 10 may then print a bottle label, for example with printer 22, and/or a shipping label, for example with printer 20. According to some embodiments of the present invention, the kiosk 10 accesses stored information about the shipping destination based on the medicine information entered initially by the user and prints the shipping destination on the shipping label. According to some embodiments of the present invention, the bottle label includes information about the type of medicine and the number of pills counted by the fiber optic sensor 62.

FIG. 7 illustrates that the drive tube 46 may include an inner diameter of 1.58 inches, and an outer diameter of 1.78 inches, according to embodiments of the present invention. The length of the drive tube 46 may be ten inches, according to embodiments of the present invention. The pitch of the flute 51 may vary, and may be, for example, from 1.4 to 2.0 per inch. The height of the flute 51 may vary, and may be, for example, from 0.1 to 0.2 inches tall above the inner diameter of the drive tube 46. According to some embodiments, the incline of the central axis 49 of the drive tube with respect to the horizontal (i.e. the ground surface horizontal level) is adjustable, for example from eight degrees to twenty degrees. Adjusting this incline angle permits the drive tube 46 to better accommodate pills of different shapes and/or sizes, to encourage them to more reliable fall out of the exit opening 50 one at a time. The incline angle of the drive tube 46 may be adjusted manually, for example during maintenance and/or manufacture, or it may be adjusted manually by the user, it may be adjusted automatically by the kiosk 10 based on known information about pill size and shape based on the user-entered information, and/or it may be adjusted responsively based on performance of the drive tube 46 (e.g. the incline may be raised if camera 58 observes an undesirable stacking or bunching up of pills along the drive tube 46), according to embodiments of the present invention. The incline of the drive tube 46 may be raised or lowered with a solenoid or stepper motor or other drive tube incline adjustment mechanism 66 controlled by the kiosk 10, according to embodiments of the present invention.

The arrangement and layout of the kiosk 10 with the pill drop opening 12 at the top, the pill chute 40 in back, and the incline of the drive chute 46 rising from back-to-front of the kiosk permits the counted pills to be conveniently gathered in the catch bin 24 which is directly in front of an accessible to the user from the same side of kiosk 10 as they are facing to interact with the touch screen 14, according to embodiments of the present invention. This arrangement saves time and money. According to embodiments of the present invention, the kiosk 10 is used by a pharmacist or other authorized handler of medicines, according to embodiments of the present invention.

Figure 8:
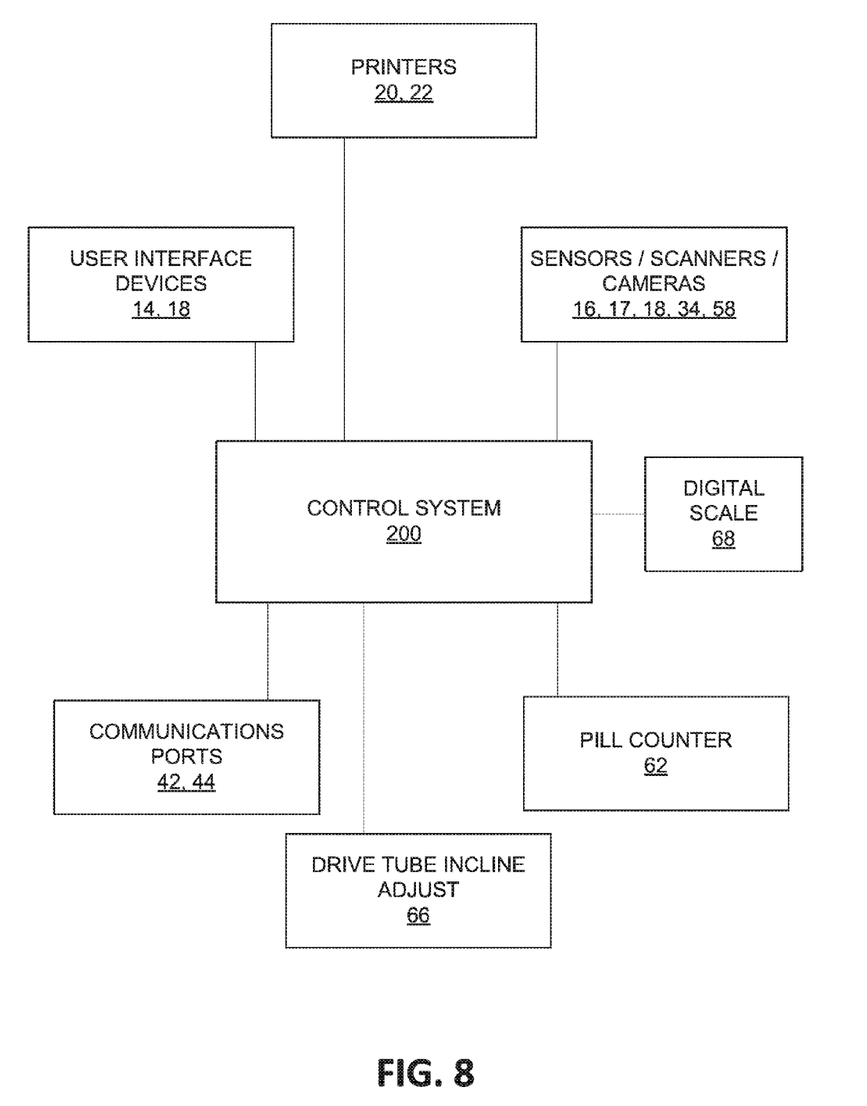
FIG. 8 illustrates a kiosk system, according to embodiments of the present invention.

FIG. 8 illustrates kiosk control system, according to embodiments of the present invention. A control system 200 is communicably coupled to user interface devices 14, 18, printers 20, 22, sensors, scanners, and cameras 16, 17, 18, 34, and 58, pill counter 62, communications ports 42, 44, drive tube incline adjustment mechanism 66, and/or digital scale 68, according to embodiments of the present invention.

Control system 200 may be a personal computer or other computing device, according to embodiments of the present invention.

The control system 200 is capable of executing instructions to perform the steps and methods described herein, in whatever order, and excluding one or more steps and/or including one or more additional steps or repetitions of steps, according to embodiments of the present invention. The control system 200 receives information or signals and, based on such information or signals, sends out control signals to cause the hardware to operate accordingly, as described herein. The control system may also receive information from other hardware, not shown. The control system 200 may also rely on other sensors or signals not expressly shown, but which are apparent to one of ordinary skill in the art based on the present disclosure. For example, positional sensors may be used to provide the control system 200 with the two-dimensional (or three-dimensional) position of any piece of hardware described herein.

Figure 9:
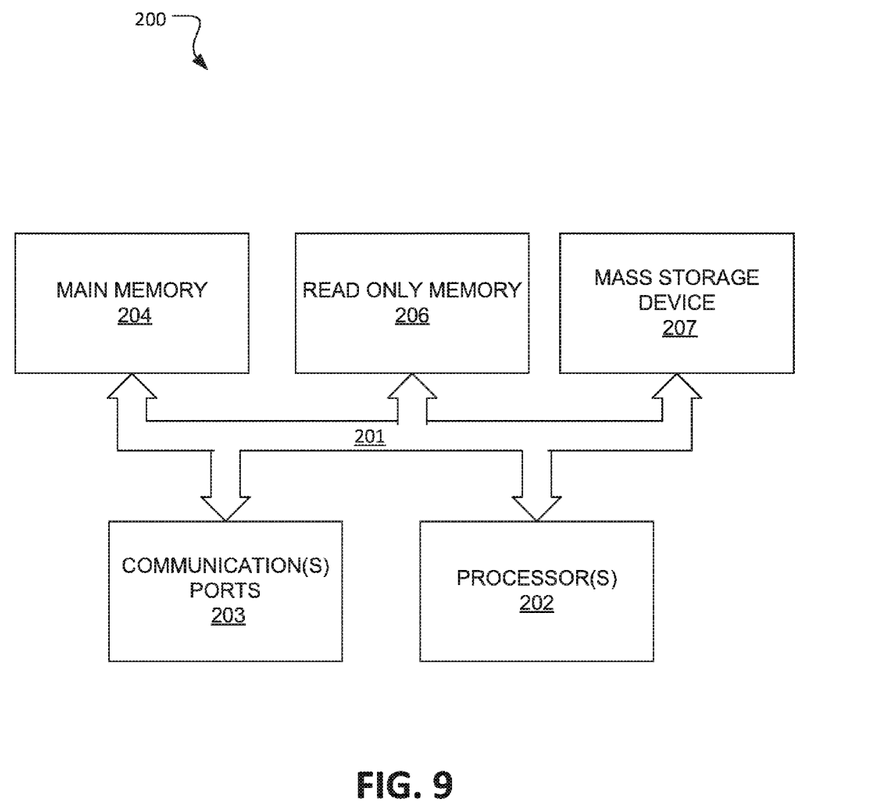
FIG. 9 illustrates a computer system, according to embodiments of the present invention.

FIG. 9 is an example of a computer system 200 with which embodiments of the present invention may be utilized. Computer system 200 represents an exemplary computer, which may operate as controller 200 in order to receive inputs (e.g. from sensors) and/or provide outputs (e.g. to control the printers, rotation of the drive tube 46, and/or incline of the drive tube 66). In this simplified example, the computer system 200 comprises a bus 201 or other communication means for communicating data and control information, and one or more processing devices 202, such as a well known processor, Application Specific Integrated Circuit (ASIC), a field programmable gate array (FPGA), or the like, coupled with bus 201.

In this simplified embodiment, computer system 200 further comprises a random access memory (RAM) or other dynamic storage device (referred to as main memory 204), coupled to bus 201 for storing information and instructions to be executed by processing device 202. Main memory 204 also may be used for storing temporary variables or other intermediate information during execution of instructions by processor(s) 202.

Computer system 200 can also include a read only memory (ROM) 206 and/or other static storage device coupled to bus 201 for storing static information and instructions for processing device 202. A mass storage device 207, such as a magnetic disk or optical disc and its corresponding drive, may also be coupled to bus 201 for storing instructions and information, such as configuration files, a key store and registration database, and the like.

One or more communication ports 203 may also be coupled to bus 201 for supporting network connections and communication of information to/from the computer system 200 by way of a communication network, such as a Local Area Network (LAN), Wide Area Network (WAN), or the Internet, for example. The communication ports 203 may include various combinations of well-known interfaces, such as one or more modems to provide network access, one or more 10/100 Ethernet ports, one or more Gigabit Ethernet ports (fiber and/or copper), or other well-known network interfaces commonly used in internetwork environments. In any event, in this manner, the computer system 200 may be coupled to a number of other network devices, communication devices, clients, NTMs, and/or servers via a conventional communication network infrastructure. Optionally, operator and administrative interfaces (not shown), such as a display, keyboard, and a cursor control device, may also be coupled to bus 201 to support direct operator interaction with computer system 200. Other operator and administrative interfaces can be provided through network connections connected through communication ports 203. Finally, removable storage media (not shown), such as one or more external or removable hard drives, tapes, floppy disks, magneto-optical discs, compact disk-read-only memories (CD-ROMs), compact disk writable memories (CD-R, CD-RW), digital versatile discs or digital video discs (DVDs) (e.g., DVD-ROMs and DVD+RW), Zip disks, or USB memory devices, e.g., thumb drives or flash cards, may be coupled to bus 201 via corresponding drives, ports or slots.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A kiosk comprising:
   a housing;
   a touch screen mounted to the housing that is configured to receive input information, wherein the input information relates to pills;
   a label printer mounted to the housing that is configured to print output information, wherein the output information relates to the pills;
   a pill drop opening;
   a pill chute in communication with the pill drop opening;
   a drive tube having an entry opening and an exit opening, wherein the drive tube is tubular, wherein the exit opening is higher than the entry opening such that a longitudinal axial centerline of the drive tube is inclined, wherein an inside surface of the drive tube comprises a helical flute, wherein the entry opening is in communication with the pill chute, and wherein an amount that the longitudinal axial centerline of the drive tube is inclined is adjustable relative to the housing;
   a motor configured to rotate the drive tube to separate and convey the pills received through the pill drop opening and the pill chute; and
   an optical counter configured to count the pills as the pills fall from the exit opening of the drive tube.

2. The kiosk of claim 1, further comprising a processor within the housing that is communicably coupled to the touch screen, the label printer, the motor, and the optical counter, wherein the processor is configured to:
   receive the input information from the touch screen;
   selectively actuate the motor to convey the pills from the entry opening to the exit opening;
   receive and store count information about a number of the pills from the optical counter; and
   cause the label printer to print a label displaying the output information, wherein the output information comprises the count information.

3. The kiosk of claim 2, further comprising:
   a camera; and
   a scale,
   wherein the processor is communicably coupled to the camera and the scale and is further configured to:
      receive information about a liquid medicine from the touch screen;
      receive and store information about a weight of the liquid medicine from the scale;

receive and store visual information from the camera about the liquid medicine while the liquid medicine is placed upon the scale; and verify the information about the weight of the liquid medicine based on the visual information.

4. The kiosk of claim 3, wherein the processor is further configured to determine whether a seal of a container containing the liquid medicine is damaged or opened.

5. The kiosk of claim 1, wherein the longitudinal axial centerline of the drive tube is inclined along a direction from a rear of the kiosk toward a front of the kiosk.

6. The kiosk of claim 5, wherein the touch screen is located at the front of the kiosk.

7. The kiosk of claim 6, further comprising a catch bin located at the front of the kiosk, wherein the catch bin is configured to receive the pills after the pills have fallen from the exit opening of the drive tube.

8. The kiosk of claim 1, wherein the output information comprises the input information and a number of pills counted by the optical counter.

9. The kiosk of claim 1, wherein the amount that the longitudinal axial centerline of the drive tube is inclined is adjustable between eight degrees and twenty degrees with respect to a horizontal aspect of the housing.

10. The kiosk of claim 1, further comprising an incline adjustment mechanism that is configured to adjust the amount that the longitudinal axial centerline of the drive tube is inclined.

11. The kiosk of claim 10, further comprising a processor communicably coupled to the touch screen and the incline adjustment mechanism, wherein the processor is configured to:

receive the input information from the touch screen;
determine a pill size of the pills based on the input information; and
cause the incline adjustment mechanism to adjust the amount that the longitudinal axial centerline of the drive tube is inclined based on the pill size.

12. The kiosk of claim 1, further comprising an endoscope camera configured to capture images of a portion of the inside surface of the drive tube.

13. The kiosk of claim 12, further comprising a processor communicably coupled to the optical counter and the endoscope camera, wherein the processor is configured to verify a number of pills counted by the optical counter based on images received from the endoscope camera.

14. A method comprising:

receiving, from a user interface, input information related to pills;
determining a size of the pills based on the input information; and
causing an adjustment mechanism to adjust an amount of an incline of a drive tube based on the size of the pills;
causing a drive motor to rotate the drive tube, wherein rotating the drive tube causes pills dropped into the drive tube to separate and to be conveyed along the incline of the drive tube, and wherein rotating the drive tube causes the pills to be dropped past an optical counter;
receiving, from the optical counter, an indication of a number of pills that dropped past the optical counter; and
causing a label printer to print a label comprising output information, wherein the output information comprises the number of pills and at least a portion of the input information.

15. The method of claim 14, further comprising:

receiving, from a scale, an indication of a weight of a liquid;
receiving, from a camera, an image of a container of the liquid, wherein the container comprises a seal;
determining, based on the image, whether the seal is damaged or opened; and
causing the label printer to print a label comprising the indication of the weight of the liquid and whether the seal is damaged or opened.

16. The method of claim 14, further comprising:

receiving, from a scale, an indication of a weight of a liquid;
receiving, from a camera, an image of a container of the liquid;
verifying, based on the image, the weight of the liquid; and
causing the label printer to print a label comprising the indication of the weight of the liquid.

17. The method of claim 14, further comprising:

receiving, from an endoscope camera, an image of a portion of an inside surface of the drive tube and a portion of the pills;
determining a number of pills based on the image; and
verify the number of pills received from the optical counter with the number of pills determined based on the image.

18. The method of claim 14, further comprising:

receiving, from an endoscope camera, an image of a portion of an inside surface of the drive tube and a portion of the pills;
determining, based on the image, that the pills are stacking up along the drive tube; and
causing an adjustment mechanism to adjust an amount of the incline of the drive tube based on the determination that the pills are stacking up.

* * * * *